United States Patent [19]

Makovec et al.

[11] Patent Number: 4,769,389
[45] Date of Patent: Sep. 6, 1988

[54] OXYGENATED-ALKYL DERIVATIVES OF GLUTAMIC AND ASPARTIC ACIDS WITH ANTAGONISTIC ACTIVITY TO BIO-ACTIVE POLYPEPTIDES AND A METHOD FOR THEIR PREPARATION

[75] Inventors: Francesco Makovec; Rolando Chiste'; Lucio Rovati; Luigi Rovati, all of Monza, Italy

[73] Assignee: Rotta Research Laboratories, S.p.A., Milan, Italy

[21] Appl. No.: 942,751

[22] Filed: Dec. 17, 1986

[30] Foreign Application Priority Data

Dec. 17, 1985 [IT] Italy ............... 68062A/85

[51] Int. Cl.$^4$ .......................... A61R 31/195
[52] U.S. Cl. ................... 514/563; 562/449; 562/450; 514/510
[58] Field of Search .......... 562/450, 449, 448; 514/563

[56] References Cited

U.S. PATENT DOCUMENTS

| | | | |
|---|---|---|---|
| 3,465,081 | 9/1969 | Fuhlhage ............... | 514/563 |
| 3,739,013 | 6/1973 | Picciola et al. ........ | 562/450 |
| 4,243,678 | 1/1981 | Krastinat ............... | 514/563 |

FOREIGN PATENT DOCUMENTS 1108819 4/1968 United Kingdom ............ 514/563

*Primary Examiner*—James H. Reamer
*Attorney, Agent, or Firm*—Sughrue, Mion, Zinn, Macpeak & Seas

[57] ABSTRACT

New Orginal derivates of D,L-glutamic acid and D,L-aspartic acid are described having the formula:

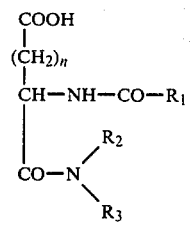

where n is 1 or 2, $R_1$ is a mono- or di-substituted phenyl group substituted with halogens such as chlorine and fluorine or with a methyl group in the 3 and 4 positions and in which $R_2$ consists of a linear or branched alkyl group with 4 to 7 carbon atoms (preferably a pentyl group) and $R_3$ is an alkyl group having 3 to 6 carbon atoms overall and containing an oxygen atom in the form of an either linkage, such as for example the groups 2-ethoxyethyl, 3-methoxypropyl, 3-ethoxypropyl etc. or in the form of a hydroxyl group such as for example 3-hydroxypropyl etc.

The compounds have antagonistic activity towards bio-active polypeptides and are usable particularly in the treatment of illnesses of the digestive tract, of the central nervous system and anorexia and of all those affections (for example tumours) in which exogenic or endogenic bio-active polypeptides are involved.

11 Claims, No Drawings

OXYGENATED-ALKYL DERIVATIVES OF GLUTAMIC AND ASPARTIC ACIDS WITH ANTAGONISTIC ACTIVITY TO BIO-ACTIVE POLYPEPTIDES AND A METHOD FOR THEIR PREPARATION

The present invention relates to novel derivatives of D,L-glutamic acid and D,L-aspartic acid which may be represented by the general formula given below

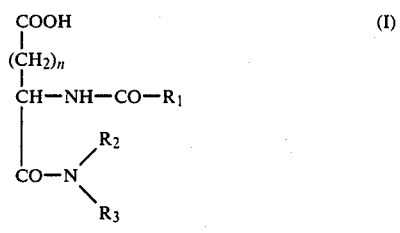

where n is 1 or 2, $R_1$ is a mono- or di-substituted phenyl group substituted with halogens such as chlorine and fluorine or with a methyl group in the 3 and 4 positions, $R_2$ consists of a linear or branched alkyl group with 4 to 7 carbon atoms (preferably a pentyl group) and $R_3$ is an alkoxyalkyl group or a hydroxyalkyl group having 3 to 6 carbon atoms overall.

Preferably $R_3$ is selected from the group consisting of 2-ethoxyethyl, 3-methoxypropyl, 3-ethoxypropyl and 3-hydroxypropyl.

The compounds of the present invention are shown to possess interesting pharmacological properties with regard to living organisms, properties which may be attributed to a powerful antagonistic activity towards cholecystokinin (CCK) or other bioregulatory peptides shown by many of the compounds in question.

The compounds of the invention may thus be used with advantage in the treatment of various illnesses in man, such as illnesses of the digestive tract, and thus may be used for example in the treatment of colitis, biliary diskinesia and in pancreatitis.

In view of their pharmacological characteristics, their use may also be envisaged in the treatment of mental disorders imputable to deficiencies in the physiological neuron levels of CCK or of other bio-active polypeptides, and also in the treatment of anorexia or to promote weight increase in livestock or for the treatment of affections in which a pathological cellular growth is mediated by bio-active peptides (probably such as various tumours).

The compounds of the invention, as already mentioned above, have a powerful anti-CCK activity on various experimental models both in vivo and in vitro. Thus they reduce the contractions induced by CCK in the gallbladder of guinea pigs both in vitro and in vivo and inhibit contractions induced in the colon in rabbits.

Their protective action against pancreatitis induced experimentally by curulein and induced by sodium taurocholate is also particularly powerful.

Pharmaceutical forms of the compounds of the invention may be prepared by conventional techniques, in the form for example of tablets, capsules, suspensions, solutions and suppositories and may be administered orally, parenterally or into the rectum.

The active ingredient is administered to the patient typically in a ratio of from 0.1 to 10 mg/kg of bodyweight per dose. For parenteral administration, it is preferable to use a water soluable salt of the compounds in question such as the sodium salt or another salt which is non-toxic and pharmaceutically acceptable. Substances commonly used in the pharmaceutical industry as excipients, binders, flavourings, dispersants, colouring agents, humectants etc. may be used as inactive ingredients.

The method for the preparation of the derivatives of glutamic acid and aspartic acid according to the invention is characterised in that it includes the step of:

(a) reacting an internal anhydride of formula (II)

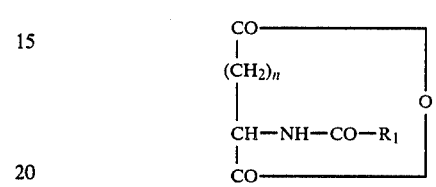

in which n and $R_1$ have the meanings given above, with an amine of formula

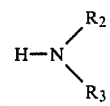

in which $R_2$ and $R_3$ have the meanings indicated above in a molar ratio of from 1 to 5 at a temperature of from $-10°$ C. to $+10°$ C. and recovering the compounds (I) from the reaction mixture.

The internal anhydrides of formula II are compounds which have already previously been described in the literature (Italian application Nos. 67644-A/84 and 68070-A/84) while most of the amines of formula

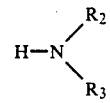

are new compounds which have not hitherto been synthesised.

The series of steps of the method of the invention is illustrated in its entirety in the following scheme.

REACTION SCHEME

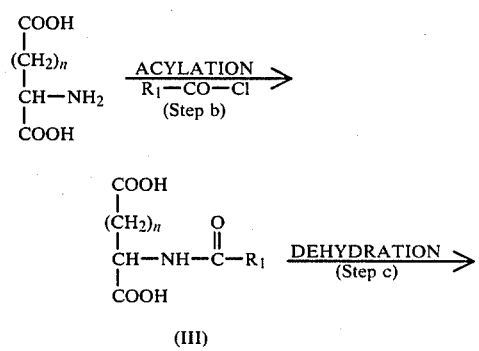

-continued
REACTION SCHEME (II) [structure: cyclic anhydride with (CH$_2$)$_n$, NH—C(=O)—R$_1$]

$$\xrightarrow[\text{(Step a)}]{\text{AMIDATION}} \quad HN\begin{smallmatrix}R_2\\R_3\end{smallmatrix}$$

(I) [structure: COOH—(CH$_2$)$_n$—CH(NH—C(=O)—R$_1$)—C(=O)—N(R$_2$)(R$_3$)]

The acylation step b is carried out at a temperature of about 5° C. over a period of from 1 to 24 hours, preferably 12 hours.

In step c, the reaction time is typically from about 30 minutes to 12 hours, preferably about 3 hours, and the quantity of acetic anhydride is preferably 3 moles per mole of compound (III).

In the amidation step, the amine of formula $$H-N\begin{smallmatrix}R_2\\R_3\end{smallmatrix}$$

is preferably introduced in a molar ratio of 2.5 to 1 with reference to the internal anhydride (II) and the reaction is carried out for a period of from about 30 minutes to 12 hours, preferably 3 hours.

The amines of formula $$H-N\begin{smallmatrix}R_2\\R_3\end{smallmatrix}$$

in which R$_2$ is a linear or branched alkyl chain containing from 5 to 7 carbon atoms and R$_3$ is an alkoxy-alkyl group have hitherto never been synthesised.

The general method of preparation of the amines of formula $$H-N\begin{smallmatrix}R_2\\R_3\end{smallmatrix}$$

is to react an excess (preferably from 2 to 3 times in moles) of a primary hydroxyalkylamine or alkoxyalkylamine of formula $$H-N\begin{smallmatrix}H\\R_3\end{smallmatrix}$$

such as for example methoxypropylamine with one mole of the corresponding alkyl halide such as for example n-pentyl bromide in a polar or apolar solvent, preferably an alcohol such as isopropyl alcohol, for a period of between 1 and 24 hours, preferably 8 hours at the reflux temperature of the solvent used.

Subsequently the amine is isolated in the pure form from the reaction mixture by fractional distillation under vacuum.

The following examples are given below better to illustrate the invention.

EXAMPLE 1

Preparation of D,L-4-(3,4-dichlorobenzoylamino)-5[N-3-methoxypropyl)-pentylamino]-5-oxo-pentanoic acid (compound 1 in Table 1)

30.2 g (0.1 moles) of 3,4-dichloro-benzoyl-glutamic anhydride are loaded into a reactor and suspended in 100 ml of water. The suspension is cooled to about 5° C. and 32.2 g (0.25 moles) of N-pentyl-N-(3-methoxypropyl)amine are added dropwise over a period of about 15 minutes.

This is left to react for three hours at this temperature then acidified with glacial acetic acid. It is filtered, washed with water until neutral and dried.

Thus 23.5 g are obtained. Yield 50.9%.

M.P.: 113°–5° C. (crystallised from acetone). TLC. RF: 0.83 (isoamyl-acetone-H$_2$O:5/2/2).

All the compounds of formula (I) are synthesised by the same procedure (see previous scheme).

Numerous examples of these compounds with several characteristics which identify them as well as the yields obtained are given by way of example in the following Table 1.

TABLE 1

Derivatives of formula

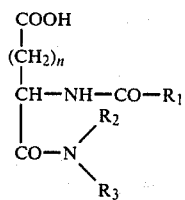

| COMPOUNDS | n | $R_1$ | $R_2$ | $R_3$ | MELTING POINT (°C.) | SOLVENT OF CRYSTALLISATION | $Rf^*$ | YIELD (%) | FORMULA |
|---|---|---|---|---|---|---|---|---|---|
| 1 | 2 | 3,4-dichloro-phenyl | pentyl | 3-methoxy-propyl | 113–5 | Acetone | 0.83 | 50.9 | $C_{21}H_{30}Cl_2N_2O$ |
| 2 | 2 | 3,4-dichloro-phenyl | pentyl | 2-ethoxy-ethyl | 125–32 | Ethanol/water 2:1 | 0.85 | 41.1 | $C_{21}H_{30}Cl_2N_2O$ |
| 3 | 2 | 3,4-dichloro-phenyl | pentyl | 3-ethoxy-propyl | 94–6 | Ethanol/water 2:1 | 0.87 | 25.5 | $C_{22}H_{32}Cl_2N_2O$ |
| 4 | 2 | 3,4-dichloro-phenyl | pentyl | 3-isopropyloxy-propyl | 88–91 | Ethanol/water 3:1 | 0.88 | 19.4 | $C_{23}H_{34}Cl_2N_2O$ |
| 5 | 2 | 3,4-dichloro-phenyl | pentyl | 2-methoxy-ethyl | 124–6 | Ethanol/water 3:1 | 0.62 | 26.0 | $C_{20}H_{28}Cl_2N_2O$ |
| 6 | 2 | 3,4-dichloro-phenyl | pentyl | 3-hydroxy-propyl | 62–5 | Ethanol/water 1:1 | 0.44 | 12.3 | $C_{20}H_{28}Cl_2N_2O$ |
| 7 | 2 | 3,4-dimethyl-phenyl | pentyl | 3-methoxy-propyl | 92–4 | Isopropyl ether | 0.76 | 23.8 | $C_{23}H_{36}N_2O_5$ |
| 8 | 2 | 3,4-dimethyl-phenyl | pentyl | 2-ethoxy-ethyl | 105–8 | Isopropyl ether | 0.79 | 32.6 | $C_{23}H_{36}N_2O_5$ |
| 9 | 2 | 4-methyl-phenyl | pentyl | 3-methoxy-propyl | 86–8 | Ethyl acetate | 0.74 | 49.2 | $C_{22}H_{34}N_2O_5$ |
| 10 | 2 | 3-methyl-phenyl | pentyl | 3-methoxy-propyl | 78–81 | Ethyl acetate | 0.71 | 61.5 | $C_{22}H_{34}N_2O_5$ |
| 11 | 2 | 4-chloro-phenyl | pentyl | 3-methoxy-propyl | 106–9 | Ethanol/water 2:1 | 0.77 | 37.9 | $C_{21}H_{31}ClN_2O_5$ |
| 12 | 2 | 4-chloro-phenyl | pentyl | 2-ethoxy-ethyl | 117–20 | Ethanol/water 2:1 | 0.78 | 32.8 | $C_{21}H_{31}ClN_2O_5$ |
| 13 | 2 | 3-chloro-phenyl | pentyl | 3-methoxy-propyl | 98–101 | Ethanol/water 2:1 | 0.75 | 54.2 | $C_{21}H_{31}ClN_2O_5$ |
| 14 | 2 | 3,4-difluoro-phenyl | pentyl | 3-methoxy-propyl | 108–10 | Ethanol | 0.66 | 27.6 | $C_{21}H_{30}F_2N_2O_5$ |
| 15 | 2 | 3,4-dichloro-phenyl | 4-methyl-pentyl | 3-methoxy-propyl | 87–9 | Acetone/water 1:1 | 0.84 | 21.5 | $C_{22}H_{32}Cl_2N_2O_5$ |
| 16 | 2 | 3,4-dichloro-phenyl | butyl | 3-methoxy-propyl | 124–7 | Acetone | 0.72 | 62.8 | $C_{20}H_{28}Cl_2N_2O_5$ |
| 17 | 2 | 3,4-dichloro-phenyl | hexyl | 3-methoxy-propyl | 93–6 | Acetone | 0.90 | 36.7 | $C_{22}H_{34}Cl_2N_2O_5$ |
| 18 | 2 | 3,4-dichloro-phenyl | 4,4-dimethyl pentyl | 3-methoxy-propyl | 71–4 | Acetone/water 1:1 | 0.93 | 18.5 | $C_{23}H_{36}Cl_2N_2O_5$ |
| 19 | 2 | 3,4-dichloro-phenyl | 3-methyl-butyl | 3-methoxy-propyl | 104–7 | Acetone/water 1:1 | 0.86 | 32.0 | $C_{21}H_{30}Cl_2N_2O_5$ |
| 20 | 1 | 3,4-dichloro-phenyl | pentyl | 3-methoxy-propyl | 110–2 | Ethyl acetate | 0.67 | 30.8 | $C_{20}H_{28}Cl_2N_2O_5$ |
| 21 | 1 | 3,4-dimethyl-phenyl | pentyl | 3-methoxy-propyl | 87–9 | Ethanol/water 2:1 | 0.58 | 42.1 | $C_{22}H_{34}N_2O_5$ |

*The values given in the table are with reference to the eluent: isoamyl alcohol/acetone/water 5:2:1

EXAMPLE 2

Preparation of N-(3-methoxypropyl)-pentylamine (compound 1 in Table 2)

891 g (10 moles) of 3-methoxypropylamine are mixed with one liter of isopropanol at ambient temperature in a reactor. 755 g (5 moles) of n-pentyl bromide are added to the solution and then heated under reflux (about 90° C.) for 12 hours. The solvent is evaporated at a reduced pressure, the residue diluted with two liters of 2N sodium carbonate, a supernatent oil is separated and distilled at reduced pressure, the 104°–8° C./20 mmHg fraction being collected. Thus 390 g of product are obtained. Yield 73%.

Numerous examples of the N-(alkoxyalkyl)-alkylamine compounds used to synthesise the compounds of formula (I) which are the subject of the invention are given in Table 2 below together with several characteristics which identify them and the yields obtained.

N-(3-hydroxypropyl)-pentylamine was prepared in accordance with the description in the literature (J.A.C.S. 59 (1937), 2280).

TABLE 2

Amine of formula

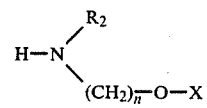

| AMINE | $R_2$ | n | $R_3$ x | BOILING POINT (Kp 20 mmHg) | YIELD (%) |
|---|---|---|---|---|---|
| 1 | pentyl | 3 | methyl | 104–8 | 73 |
| 2 | pentyl | 2 | ethyl | 95–8 | 70 |
| 3 | pentyl | 3 | ethyl | 127–9 | 75 |
| 4 | pentyl | 3 | isopropyl | 141–3 | 68 |
| 5 | pentyl | 2 | methyl | 70–3 | 65 |
| 6 | 4-methyl-pentyl | 3 | methyl | 129–31 | 68 |
| 7 | butyl | 3 | methyl | 72–4 | 59 |
| 8 | hexyl | 3 | methyl | 133–5 | 76 |
| 9 | 4,4-dimethyl-pentyl | 3 | methyl | 141–4 | 77 |
| 10 | 3-methyl-butyl | 3 | methyl | 102–4 | 72 |

The powerful anti-cholecystokinin (anti-CCK) activity displayed by many of the compounds of the invention will now be demonstrated by a series of pharmacological experiments carried out both in vitro and in vivo.

ANTI-CCK ACTIVITY ON GUINEA-PIG GALLBLADDERS IN VITRO

A longitudinal strip of guinea-pig gallbladder is placed in a bath for isolated organs in Krebs at a temperature of 32° C. and oxygenated continuously with an oxygen-$CO_2$ mixture (95–5 V/V).

The isometric contractions were detected by means of a force transducer and recorded.

The gallbladder was contracted with the use of a 10 ng/ml concentration of CCK-8; the antagonistic activity of the compounds of the invention towards the contracting effect of CCK was determined with the use of different concentrations so as to determine the value of the IC50, that is the concentration in mcg/ml of compound with a 50% antagonising effect on the contracting effect of CCK.

The results obtained are shown in Table 3 which gives the compounds tested and the IC50 values found which were calculated by the method of regression in a test of at least three experiments for each compound studied.

TABLE 3

Anti-CCK-8 activity (concentration used: 10 ng/ml) of the compounds of the invention on guinea-pig gall bladders in vitro expressed as the IC50 in mcg/ml.

| COMPOUNDS | ACTIVITIES IC50 (mcg/ml) |
|---|---|
| 1 | 0.1 |
| 2 | 0.1 |
| 3 | 0.6 |
| 4 | 3.0 |
| 5 | 0.8 |
| 6 | 0.3 |
| 7 | 0.9 |
| 8 | 1.1 |
| 9 | 4.0 |
| 10 | 4.1 |
| 11 | 2.6 |
| 12 | 2.9 |
| 13 | 8.9 |
| 14 | 0.8 |
| 15 | 0.7 |
| 16 | 1.5 |
| 17 | 1.6 |
| 18 | 4.8 |
| 19 | 0.6 |
| 20 | 0.9 |
| 21 | 4.7 |
| Proglumide | 340.0 |

From the data given in the table it is seen that the claimed compounds have a 50% antagonising effect on the activity of CCK-8 at a concentration which, for the most active compounds (such as for example the compounds 1 and 2), is only about 10 times greater than that of the specific agonist, thus showing an extremely high specificity of action. Moreover the chosen compound for comparison, proglumide, which is the most notable of the known drugs with anti-CCK activities, has an activity of about 3000 times less in this test than that of the most active compound in the invention.

In order to confirm the evidence of the studies in vitro, several of the more interesting compounds were tested in vivo with the use of guinea-pig gallbladders in situ.

The method used was that described by Ljungberg (Svensk. Farm. Tidskr. 69, 351–354, 1964).

Guinea-pigs having a weight of about 400 g anaesthetised with urethane were used; the substances being tested were administered intravenously (i.v.) into the jugular vein.

The responses of the gallbladder to the substances being tested were detected by means of a force transducer and recorded by means of a microdynamometer. 10 ng/kg of CCK 8 were chosen as the optimum contracting dose. The antagonistic compounds tested were administered in increasing doses so as to enable the calculation of an ID50 value, that is the dose (in mg/kg i.v.) having a 50% inhibiting effect against contractions induced by 10 ng/kg i.v. of CCK-8.

The results obtained are illustrated in Table 4 below which gives the effect obtained expressed as the ID50

TABLE 4

Anti-CCK-8 activity (concentration used: 10 ng/kg) of several of the compounds of the invention on guinea pig gall bladders "in situ", expressed as the ID50 in mg/kg i.v. in comparison with proglumide.

| COMPOUNDS | ID50 (mg/kg/i.v.) |
|---|---|
| 1 | 0.11 |
| 2 | 0.10 |
| 3 | 0.75 |
| 4 | 5.08 |
| 5 | 0.68 |
| 6 | 8.40 |
| 7 | 0.65 |
| 8 | 2.02 |
| 9 | 3.85 |
| 10 | 3.66 |
| 11 | 3.25 |
| 12 | 4.44 |
| 13 | 6.70 |
| 14 | 1.10 |
| 15 | 0.84 |
| 16 | 2.08 |
| 17 | 3.25 |
| 18 | 6.79 |
| 19 | 0.74 |
| 20 | 0.84 |
| 21 | 3.69 |
| Proglumide | 70.5 |

The results thus obtained substantially confirm what had already been seen in the experiments in vitro, that is that several of the compounds of the invention are extremely powerful CCK atagonists, capable of blocking contractions of the gallbladder induced by CCK-8 administered at concentrations considerably above those which induce pathological syndromes at doses of about 0.1 mg/kg (in the case of compounds 1 and 2). The compounds tested were also considerably more active than the control drug proglumide in vivo.

The anti-spastic activity which the present compounds exert on the whole of the digestive tract is also considerable. Measured in mice with the vegetable carbon test (speed of transit through the stomach and intestine) this activity is illustrated in the following table:

TABLE 5

Examples of anti-spastic activities for the claimed compounds administered intraperitoneally in mice. Values expressed as the ED50 in mg/kg, that is the dose which reduces the intestinal transit time of the carbon by 50%.

| COMPOUNDS | ANTISPASTIC ACTIVITIES ED50 mg/kg (i.p.) |
|---|---|
| 1 | 12.8 |
| 2 | 14.0 |
| 3 | 25.0 |
| 5 | 20.8 |
| 7 | 33.9 |
| 15 | 44.2 |
| 19 | 18.5 |

TABLE 5-continued

Examples of anti-spastic activities for the claimed compounds administered intraperitoneally in mice. Values expressed as the ED50 in mg/kg, that is the dose which reduces the intestinal transit time of the carbon by 50%.

| COMPOUNDS | ANTISPASTIC ACTIVITIES ED50 mg/kg (i.p.) |
|---|---|
| 20 | 27.9 |

A much more specific anti-spastic activity, that is much closer to a physiological situation is illustrated by the following experiment.

The abdomen of anaesthetised rabbit is cut open to display the tranverse colon. A small balloon full of water is inserted at an established point and connected to a pressure transducer by means of a polyethylene cannula filled with $H_2O$.

The optimum sensitivity being fixed in relation to the physiological contractions, the products were administered through the femeral vein. Contractions were induced by the administration of 100 ng/kg of CCK.

The activities of the compounds of the invention are illustrated in Table 6.

TABLE 6

Antispastic activity in the colon of rabbits stimulated with CCK-8

| COMPOUNDS | DOSES (mg/kg i.v.) | EXPERIMENT 1 | EXPERIMENT 2 | ED50 (mg/kg i.v.) r = (coeff. of correlation) |
|---|---|---|---|---|
| 1 | 0.3 | −20.8 | −34.1 | ED50 = 1.24 |
|  | 1 | −48.9 | −55.6 | r = 0.96 |
|  | 3 | −100.0 | −87.8 |  |
| 2 | 0.3 | −9.8 | −27.2 | ED50 = 1.47 |
|  | 1 | −45.1 | −39.8 | r = 0.98 |
|  | 3 | −88.0 | −92.4 |  |
| Proglumide | 25 | −33.7 | 0 | ED50 = 92.6 |
|  | 50 | −38.1 | −16.1 | r = 0.83 |
|  | 100 | −64.4 | −43.1 |  |

The data given indicate that several of the tested compounds of the present invention, as already shown for the gallbladder, also antagonise the contractions induced in the intestine by CCK administered in high doses (100 ng/kg).

The anti-spastic activity is shown at doses of about 1 mg/kg for the best of the compounds used, which is almost 100 times more active than proglumide even in this test.

Another particularly interesting pharmacological characteristic of the compounds in question which could result in a considerable therapeutic innovation is their activity on various forms of pancreatitis induced experimentally in animals by cerulein and sodium taurocolate.

The experiments where carried out as follows.

PANCREATITIS INDUCED BY CERULEIN

The method of Niedereau et al. (*Gastroenterology* 88 (1985) 1192-1204) was followed essentially.

Adult male mice received six injections of cerulein (Takus) (50 mcg/kg) each hour for six hours.

The compound was administered 30 minutes before each administration of cerulein. Nine hours after the beginning of the treatment, the blood was taken from the rectro-orbitory plexus after anaesthesia with ether, the animals were killed and the pancreas removed and weighed. The activity of the serum amylase was determined by the Ceska method (*Clin. Chim. Acta* 26 (1969) 437–444).

TABLE 7

Examples of protecting activity of the claimed compounds on pancreatitis in mice induced experimentally by cerulein

|  | % RATIO WEIGHT OF PANCREAS ANIMAL WEIGHT | % INHIBITION OF WEIGHT INCREASE (ED50 mg/kg ip) | AMYLASE IN THE SERUM (U/ml) | % INHIBITION OF WEIGHT INCREASE (ED50 mg/kg ip) |
|---|---|---|---|---|
| Controls | 0.34 | — | 11.0 | — |
| Controls + Cerulein | 0.55 | — | 90.9 | — |
| Compound 1 (5 mg/kg) + Cerulein | 0.46 | 42.8  ED50 = 5.5 (r = 0.99) | 29.4 | 76.9  ED50 = 4.2 (r = 0.95) |
| Compound 1 (7.5 mg/kg) + Cerulein | 0.40 | 71.4 | 25.6 | 81.6 |
| Compound 1 (10 mg/kg) + Cerulein | 0.36 | 90.5 | 13.2 | 97.1 |
| Controls | 0.35 | — | 10.1 | — |
| Controls + Cerulein | 0.60 | — | 109.6 | — |
| Compound 2 (5 mg/kg) + Cerulein | 0.54 | 24.5  ED50 = 6.3 (r = 0.97) | 54.7 | 55.2  ED50 = 4.6 (r = 0.99) |
| Compound 2 (7.5 mg/kg) + Cerulein | 0.45 | 61.2 | 21.7 | 88.3 |
| Compound 2 (10 mg/kg) + Cerulein | 0.38 | 89.8 | 11.8 | 98.3 |
| Controls | 0.34 | — | 11.0 | — |
| Controls + Cerulein | 0.55 | — | 90.9 | — |
| Proglumide (200 mg/kg) + Cerulein | 0.47 | 38.1  ED50 = 240.8 (r = 0.99) | 48.2 | 53.4  ED50 = 225.9 (r = 0.98) |
| Proglumide (400 mg/kg) + Cerulein | 0.37 | 85.7 | 26.2 | 80.9 |

The results obtained for several of the compounds of the invention are given in Table 7 below in comparison with those of proglumide and are expressed as the ED50, that is the quantity of substance in mg/kg i.v. having a 50% inhibiting action on the increase in weight of the pancreas and the concentration of serum amylase.

From the data given it is seen that the compounds of the invention display their protective activity on the pancreas at very low doses; the ED50 values calculated are of the order of 4 to 5 mg/kg both for inhibition of the serum amylase increase and the increase in weight of the pancreas. The control drug proglumide is also active but at considerably higher doses. The activity ratio of the most active of the drugs of the invention and proglumide in this test was in fact about 50.

PANCREATITIS INDUCED BY SODIUM TAUROCOLATE

The method described by Aho et al. (*Scandinavian J. Gastroenterology* 15 (1980), 411–16) was followed.

Male rats with a weight of about 250 g were subject to laparatomy and the pancreas displayed, 0.3 ml of a 6% solution of sodium taurocolate were injected directly into the pancreatic tissue.

The products under examination were administered intraperitoneally (i.p.) 30 minutes before the operation and 3 hours after the operation. Six hours after the laparatomy the blood was removed from the retro-orbitory plexus after anaesthesia with ether, the animals were killed and the pancreas was removed and weighed. The activity of the serum amylase was determined by the method described above.

The results obtained with the compounds 1 and 2 are given in Table 8 with comparison with those for proglumide.

is less specific. However, even in this experiment, the compounds of the invention inhibit both effects, which indicates the presence of an inflammatory process in the pancreas, at doses of between 5 and 10 mg/kg of weight.

Proglumide is active only at concentrations 30 to 60 times higher.

In order to verify the hypothesis that the anti-CCK activity manifested by most of the compounds in question may be used to advantage in the treatment of anorexia in man or as an appetite stimulant in livestock, the following experiment was carried out:

Male rats were used having an initial weight of about 160 g divided into groups of 10 animals. Each group received the drug (compound 1) in the doses indicated for three weeks daily by mouth.

The drug in the form of the sodium salt was dissolved in water and administered in a volume of 10 ml of $H_2O$/kg while the control group received an equal volume of the solvent alone.

TABLE 8

Examples of protecting activity of the claimed compounds on pancreatitis in rats induced experimentally by taurocholate.

|  | % RATIO WEIGHT OF PANCREAS ANIMAL WEIGHT | % INHIBITION OF WEIGHT INCREASE | (ED50 mg/kg ip) | AMYLASE IN THE SERUM (U/ml) | % INHIBITION OF AMYLASE INCREASE | (ED50 mg/kp ip) |
|---|---|---|---|---|---|---|
| Controls | 0.40 | — |  | 8.6 | — |  |
| Controls + Taurocholate | 0.53 | — |  | 12.0 | — |  |
| Compound 1 (5 mg/kg) + Taurocholate | 0.47 | 46.1 | ED50 = 6.9 (r = 0.95) | 10.4 | 47.0 | ED50 = 7.3 (r = 0.99) |
| Compound 1 (10 mg/kg) + Taurocholate | 0.42 | 84.6 |  | 9.8 | 64.7 |  |
| Compound 1 (20 mg.kg) + Taurocholate | 0.39 | 107.7 |  | 7.8 | 123.5 |  |
| Controls | 0.35 | — |  | 7.8 | — |  |
| Controls + Taurocholate | 0.62 | — |  | 11.7 | — |  |
| Compound 2 (5 mg/kg) + Taurocholate | 0.50 | 44.4 | ED50 = 10.1 (r = 0.89) | 10.6 | 28.2 | ED50 = 8.6 (r = 0.98) |
| Compound 2 (10 mg/kg) + Taurocholate | 0.45 | 63.0 |  | 8.9 | 71.8 |  |
| Compound 2 (20 mg/kg) + Taurocholate | 0.42 | 74.1 |  | 7.7 | 102.6 |  |
| Controls | 0.38 | — |  | 7.8 | — |  |
| Controls + Taurocholate | 0.52 | — |  | 20.1 | — |  |
| Proglumide (200 mg/kg) + Taurocholate | 0.49 | 21.4 | ED50 = 467.3 (r = 0.99) | 14.5 | 45.5 | ED50 = 222.5 (r = 0.99) |
| Proglumide (400 mg/kg) + Taurocholate | 0.46 | 42.8 |  | 9.1 | 89.4 |  |

The following tables give the average values of the food consumption and the average weight of each group of animals calculated weekly as well as the Student t value calculated between the various groups treated and the group of control animals. From the data given in Tables 9 and 10 it can be seen that daily doses of 0.625 mg/kg of the compound 1 induce an increase of about 20% in the food consumption compared with the controls; this increase is about 30% for the other doses tested and is at all times highly significant.

The increase in weight of the animals treated compared with the weight increase of the control animals is similar; all the groups treated with the compound 1 gave a significantly higher weight increase than the control animals starting from the first week of treatment.

From the data given in Table 8 it is seen that the taurocolate induces enlargement of the pancreas equivalent to that caused by CCK-8. The effect of the increase in amylase is however much less marked; it is thus clear that the mechanism of the taurocolate action

TABLE 9

Food consumption (in g/week) in the various groups treated determined at different times

| GROUPS | DOSE (mg/kg os) | 1ST WEEK | 2ND WEEK | 3RD WEEK |
|---|---|---|---|---|
| A: Control | — | 168.5 ± 1.2 | 190.8 ± 4.2 | 208.4 ± 4.1 |
| B: Compound 1 Student tvsA | 0.625 | 187.1 ± 6.3 2.88* | 220 ± 3.9 5.08*** | 242.5 ± 3.3 6.56*** |
| C: Compound 1 Student tvsA | 1.25 | 205 ± 4.6 7.82*** | 217.5 ± 3.8 4.74*** | 253.5 ± 2.4 9.6*** |
| D: Compound 1 Student tvsA | 2.5 | 209.2 ± 3.3 11.5*** | 222.2 ± 2.6 6.3*** | 270.7 ± 4.5 10.2*** |

Note:
*($P < 0.05$)
**($P < 0.01$)
***($P < 0.001$)

TABLE 10

Determination of body weight (in g) of the various groups measured at different times

| GROUPS | DOSE (mg/kg os) | TIME 0 | 1ST WEEK | 2ND WEEK | 3RD WEEK |
|---|---|---|---|---|---|
| A: Controllo | — | 166.4 ± 1.8 | 204.5 ± 2.5 | 246.9 ± 2.1 | 287 ± 2.5 |
| B: Compound 1 Student tvsA | 0.625 | 169.3 ± 1.9 1.1 | 216.9 ± 3.8 2.71* | 267.5 ± 3.9 4.59*** | 324 ± 3.6 8.35*** |
| C: Compound Student tvsA | 1.25 | 168.3 ± 1.1 0.8 | 242.7 ± 4.9 6.05*** | 318.3 ± 4.4 14.66*** | 371 ± 5.6 13.6*** |
| D: Compound Student tvsA | 2.5 | 165.8 ± 1.3 0.27 | 241.6 ± 3.7 8.25*** | 325.2 ± 5.5 13.3*** | 374.9 ± 5.1 15.2*** |

Note:
*(P < 0.05)
**(P < 0.01)
***(P < 0.001)

INHIBITING ACTION ON THE RATE OF GROWTH OF A PANCREATIC ADENOCARCINOMA INDUCED BY CCK-8

It was desired to study the effect of one of the more active of the compounds claimed such as anticholecystokinin, that is compound 1, on the trophic activity of CCK on normal pancreatic cells and on those of a pancreatic adenocarcinoma.

Male hamsters were innoculated in the cheek pouch with a suspension of $1 \times 10^5$ tumour cells of a pancreatic adenocarcinoma. Five days after the innoculation the animals were divided at random into four groups of 10 animals, that is a control group, a group of animals treated with 8 mcg/kg of CCK-8 three times a day, a group of animals treated with 4 mg/kg i.p. doses of compound 1 three times a day, and a fourth group treated simultaneously with the compound 1 and with CCK-8 in the manner indicated above.

Fifteen days after this treatment the animals were killed and the normal pancreas and the pancreatic tumours initiated in the cheek pouch were removed and weighed.

The DNA was extracted and measured by conventional methods.

The results obtained are given in Table 11 in which they are expressed as average values ± S.E.

The data given in the table show how the hormone cholecystokinin (of which CCK-8 is the biologically active component) which has a trophic action on normal pancreatic cells also stimulates the growth of a pancreatic adenocacinoma. The compound 1 atagonises both these actions of CCK-8 to a highly significant extent.

The experimental data set out above would seem to indicate that the use of the compound 1 or other anticholecystokinin compounds of the invention could be particularly favourable in the treatment of tumours sustained by endogenous bio-active polypeptides (particularly CCK) such as pancreatic tumours and gastrointestinal tumours.

TOXICITY AND TOLERABILITY IN ANIMALS

The substances of the present invention have been shown to have relatively low toxicities and be well tolerable, if their activities and their likely dosage levels in man are taken into account.

Table 12 gives the LD50 values in mice for intravenous injection (i.v.), that is the dose of the drug which causes the death of 50% of the animals treated, for several of the more interesting compounds and a therapeutic index which takes account both of the anti-CCK activity in vivo and the toxicity of the compounds, that is the ratio between the LD50 values of the products and the corresponding ED50 values taken from Table 4.

TABLE 11

Inhibiting action of compound 1 on the growth rate induced by CCK-8 on normal and tumoral pancreatic cells in hamsters

| TREATMENT | DOSE | WEIGHT OF THE PANCREAS (mg) | Student t | PANCREATIC DNA (mg) | Student t | WEIGHT OF THE PANCREATIC CARCINOMA (mg) | Student t | TUMORAL DNA (mg) | Student t |
|---|---|---|---|---|---|---|---|---|---|
| A: Control | — | 377.5 ± 18.3 | | 0.79 ± 0.05 | | 112.1 ± 4.3 | | 0.4 ± 0.03 | |
| B: CCK-8 | 8 mcg/kg (3 al di) | 634.8 ± 20.8 | 9.29*** | 1.5 ± 0.06 | 8.55*** | 163.1 ± 4.7 | 7.95*** | 0.7 ± 0.03 | 5.95*** |
| C: Compound 1 | 4 mg/kg (3 al di) | 351.2 ± 17.2 | 1.05 | 0.78 ± 0.03 | 0.2 | 105.0 ± 4.1 | 1.19 | 0.42 ± 0.03 | 0.33 |
| D: Compound 1 + CCK-8 | 8 mcg/kg CCK-8 + 4 mg/kg Compound 1 | 370.2 ± 12.7 | vsA: 0.33 vsB: 10.87*** | 0.83 ± 0.06 | vsA: 0.45 vsB: 7.97*** | 108.8 ± 5.4 | vsA: 0.47 vsB: 7.53*** | 0.44 ± 0.03 | vsA: 0.97 vsB: 5.53*** |

Note:
*(P = <0.01)
**(P = <0.001)

TABLE 12

Toxicity, anti-CCK activity in vivo and relative therapeutic indices.

| COM-POUND | DL50 IN (mg.kg i.v.) | ANTI-CCK ACTIVITY(*) IN VIVO IN GUINEA PIGS ED50 mg/kg i.v. | THERA-PEUTIC INDEX DL50/ED50 |
|---|---|---|---|
| 1 | 396 | 0.11 | 3600 |
| 2 | 338 | 0.10 | 3380 |
| 3 | 298 | 0.75 | 397 |
| 5 | 485 | 0.68 | 713 |
| 7 | 440 | 0.65 | 677 |
| 14 | 425 | 1.10 | 386 |
| 15 | 288 | 0.84 | 343 |
| 19 | 297 | 0.74 | 401 |
| 20 | 362 | 0.84 | 431 |
| Proglumide | 2400 | 70.5 | 34 |

(*)Values drawn from table 4

From the results given in Table 12 it is seen that the more active of the compounds claimed have a relatively high safety margin shown by the difference between the acute toxicity values and the very high pharmacological activities. These safety margins have been evaluated by us as the therapeutic index which is extremely high for the more active compounds (greater than 3000).

From the data given it is also seen that the therapeutic index of the compounds of the invention is from 10 to 100 times greater than that of proglumide.

The compounds of the invention are also very well tolerated in parenteral administration. For example compound 1 which as the highest therapeutic index may be injected intravenously in aqueous solution in the form of the sodium salt into the test animals up to a concentration of 1.5 percent (volume injected: 10 ml/kg equivalent to 150 mg/kg) without causing haemolysis nor variations in the haematocrit.

The compound does not moreover give rise to tissue damage at this concentration when injected subcutaneously.

The experimental data given above have thus demonstrated the possible utility of these compounds in the treatment of various pathological conditions which concern the gastrointestinal tract, for example in spastic syndromes and pain in general such as biliary diskinesia or irritable colon.

The use of these products for the treatment of pancreatitis could be particularly advantageous, since reliable active drugs the effectiveness of which has been shown by appropriate pharmacological tests are unknown for this pathological condition.

Equally advantageous could be the treatment of tumours sustained by endogenous bio-active polypeptides such as for example CCK.

It is also possible to envisage a favourable therapeutic use for many of the compounds in question for the treatment of various forms of anorexia and also in the treatment of several pathological conditions of the CNS linked to deficiencies in the physiological neuron levels of the CCK or other bio-active peptides, both for non-serious conditions (for which the so-called tranquillising drugs are indicated) and for serious forms such as schizophrenia, or for others which in addition to the nervous system involve the muscular system, such as parkinsonism etc.

What is claimed is:

1. Pharmaceutically active derivatives of D,L-glutamic and D,L-aspartic acid having the formula:

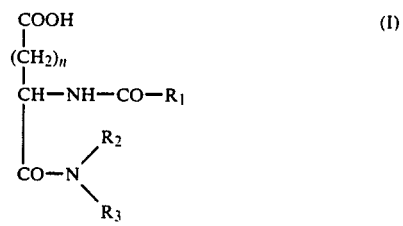

where n is 1 or 2, $R_1$ is selected from phenyl substituted with halogen in each of the 3- and 4-position or substituted with methyl in the 3-position, the 4-position, or the 3- and 4 positions, $R_2$ is selected from linear and branched alkyl groups with 4 to 7 carbon atoms and $R_3$ is selected from alkoxyalkyl and hydroxyalkyl having 3 to 6 carbon atoms overall, and their pharmaceutically-acceptable salts.

2. Derivative of D,L-glutamic acid and D,L-aspartic acid according to claim 1, in which $R_2$ is a pentyl group and $R_3$ is selected from the group consisting of 2-ethoxyethyl, 3-methoxypropyl, 3-ethoxypropyl and 3-hydroxypropyl.

3. Derivative of glutamic acid according to claim 1, in which $R_1$ is 3,4-dichlorophenyl, $R_2$ is a pentyl group and $R_3$ is a 3-methoxypropyl group.

4. A pharmaceutical composition including at least one of the compounds according to claim 1 or a pharmaceutically-acceptable salt thereof as the active ingredient.

5. A pharmaceutical composition according to claim 4 further including pharmaceutically-acceptable inactive ingredients selected from the group consisting of vehicles, binders, flavourings, dispersing agents, preservatives, humectants, and mixtures thereof.

6. A method for prevention or treatment of spasms, comprising administration of a pharmaceutical composition comprising a pharmaceutically active amount of at least one of the derivatives according to claim 1 or a pharmaceutically acceptable salt thereof in as the active ingredient in a pharmaceutically acceptable carrier.

7. A method for treatment of pancreatitis comprising administration of a pharmaceutical composition comprising a pharmaceutically active amount of at least one of the derivatives according to claim 1 or a pharmaceutically acceptable salt thereof in as the active ingredient in a pharmaceutically acceptable carrier.

8. A method for treatment of pathological conditions of the central nervous system linked to deficiencies in the physiological neuron levels of cholecystokinin or other bio-active polypeptides comprising administration of a pharmaseutical composition comprising a pharmaceutically active amount of at least one of the derivatives according to claim 1 or a pharmaceutically acceptable salt thereof in as the active ingredient in a pharmaceutically acceptable carrier.

9. A method for treatment of anorexia comprising administration of a pharmaceutical composition comprising a pharmaceutically active amount of at least one of the derivatives according to claim 1 or a pharmaceutically acceptable salt thereof in as the active ingredient in a pharmaceutically acceptable carrier.

10. A mentod for treatment of tumors in which bio-active polypeptides such as cholecystokinin and similar mechanisms are involved comprising administration of a pharmaceutical composition comprising a pharmaceutically active amount of at least one of the derivatives according to claim 1 or a pharmaceutically acceptable salt thereof in as the active ingredient in a pharmaceutically acceptable carrier.

11. A method for stimulating appetite in livestock comprising administration of a stimulant composition having as an active ingredient a derivative or pharmaceutically acceptable salt of a derivative as claimed in claim 1.

* * * * *